United States Patent
Espinosa Rueda et al.

(10) Patent No.: US 10,221,477 B2
(45) Date of Patent: Mar. 5, 2019

(54) METHOD FOR PRODUCING A HYDROGEN-DETECTION SENSOR AND RESULTING SENSOR

(71) Applicant: ABENGOA SOLAR NEW TECHNOLOGIES, S.A., Sevilla (ES)

(72) Inventors: Guillermo Espinosa Rueda, Sevilla (ES); Noelia Martinez Sanz, Sevilla (ES); Agustín Rodríguez González-Elipe, Sevilla (ES); Pedro Castillero Durán, Sevilla (ES); Ángel Barranco Quero, Sevilla (ES); Francisco Yubero Valencia, Sevilla (ES); Juan Pedro Espinos Manzorro, Sevilla (ES); José Cotrino Bautista, Sevilla (ES); Francisco García García, Sevilla (ES)

(73) Assignee: ABENGOA SOLAR NEW TECHNOLOGIES, S.A., Sevilla (ES)

( * ) Notice: Subject to any disclaimer, the term of this patent is extended or adjusted under 35 U.S.C. 154(b) by 169 days.

(21) Appl. No.: 15/024,515

(22) PCT Filed: Sep. 29, 2014

(86) PCT No.: PCT/ES2014/000157
§ 371 (c)(1),
(2) Date: Mar. 24, 2016

(87) PCT Pub. No.: WO2015/044471
PCT Pub. Date: Apr. 2, 2015

(65) Prior Publication Data
US 2016/0237556 A1 Aug. 18, 2016

(30) Foreign Application Priority Data
Sep. 30, 2013 (ES) .................................. 201300896

(51) Int. Cl.
*C23C 14/35* (2006.01)
*C23C 14/58* (2006.01)
(Continued)

(52) U.S. Cl.
CPC ........ *C23C 14/5806* (2013.01); *C23C 14/083* (2013.01); *C23C 14/226* (2013.01);
(Continued)

(58) Field of Classification Search
CPC ..... C23C 14/226; C23C 14/083; C23C 14/35; C23C 14/5806
(Continued)

(56) References Cited

FOREIGN PATENT DOCUMENTS

WO    2009133997 A1    5/2009

OTHER PUBLICATIONS

Outstanding H2 Sensing Performance of Pd Nanoparticle-Decorated ZnO Nanorod Arrays and the Temperature-Dependent Sensing Mechanisms, Chia-Ming Chang, Min-Hsiung Hon, and Ing-Chi LeuACS Applied Materials & Interfaces 2013 5 (1), 135-143 (Year: 2012).*

(Continued)

*Primary Examiner* — Rodney G McDonald
(74) *Attorney, Agent, or Firm* — Egbert Law Offices, PLLC

(57) ABSTRACT

A method is provided for producing a visual hydrogen sensor and to a sensor produced in this manner, the sensor allowing the presence of hydrogen gas in a medium to be detected by the naked eye as a result of a change of color in the sensor. The method involves the deposition of thin porous layers of oxides that do not absorb visible light in their completely oxidized state which become colored when they are partially reduced. This deposition is carried out using vapor phase deposition (PVD) in a glancing angle configuration (GLAD). The method also involves the prepa-
(Continued)

ration of a solution of an active metal precursor capable of dissociating the hydrogen molecule and a carrier vector and the deposition of this solution on the oxide layer in order to incorporate a minimum quantity of active metal within the pores of the oxide layer in the form of nanoparticles.

4 Claims, 3 Drawing Sheets

(51) Int. Cl.
| | |
|---|---|
| *G01N 33/00* | (2006.01) |
| *G01N 21/78* | (2006.01) |
| *C23C 14/08* | (2006.01) |
| *C23C 14/22* | (2006.01) |
| *G01N 31/22* | (2006.01) |

(52) U.S. Cl.
CPC ........... *C23C 14/35* (2013.01); *G01N 21/783* (2013.01); *G01N 33/005* (2013.01); *G01N 31/224* (2013.01)

(58) Field of Classification Search
USPC .................................................. 204/192.15
See application file for complete search history.

(56) References Cited

OTHER PUBLICATIONS

Hui-Feng Wang et al., Model oxide-supported metal catalysts—comparison of ultrahigh vacuum and solution based preparation of Pd nanoparticles on a single-crystalline oxide substrate, Phys. Chem. Chem. Phys., 2012, 14, 11525-11533, 2012 (Year: 2012).*

A. Wisitsoorat d al., "Optical H, sensing properties of vertically aligned Pd/W03 nanorods thin films deposited via glancing angle rf magnetron sputtering", Sensors and Actuators B: Chemical, 2013, vol. 182, pp. 795-801. (Year: 2013).*

M. U. Qadri et al., "Effed of Pt nanoparticles on the optical gas sensing properties of W03 thin film", Sensors, 2014 (accessible online Jun. 27, 2014), vol. 14, pp. 11427-11443. (Year: 2014).*

M. Ando et al., "Optical hydrogen sensitivity of noble metal-tungsten oxide composite films prepared by sputtering deposition", Sensor and Aduators B: Chemical, 2001, vol. 76, pp. 13-17. (Year: 2001).*

M. H.Yaacob et al., "Optical response of W03 nanostrudured thin films sputtered on different transparent substrates towards hydrogen of low concentration", Sensors and Actuators B: Chemical, 2013, vol. 177, pp. 981-988. (Year: 2013).*

International Search Report for corresponding International Application No. PCT/ES2014/000157.

A. Wisitsoorat ct al., "Optical H, sensing properties of vertically aligned Pd/W03 nanorods thin films deposited via glancing angle rf magnetron sputtering", Sensors and Actuators B: Chemical, 2013, vol. 182, pp. 795-801.

M. U. Qadri et al., "Effect of Pt nanoparticles on the optical gas sensing properties of WO3 thin film", Sensors, 2014 (accessible online Jun. 27, 2014), vol. 14, pp. 11427-11443.

M. Ando et al., "Optical hydrogen sensitivity of noble metal-tungsten oxide composite films prepared by sputtering deposition", Sensor and Actuators B: Chemical, 2001, vol. 76, pp. 13-17.

M. H. Yaacob et al., "Optical response of WO3 nanostructured thin films sputtered on different transparent substrates towards hydrogen of low concentration", Sensors and Actuators B: Chemical, 2013, vol. 177, pp. 981-988.

* cited by examiner

METHOD FOR PRODUCING A HYDROGEN-DETECTION SENSOR AND RESULTING SENSOR

CROSS-REFERENCE TO RELATED U.S. APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

BACKGROUND OF THE INVENTION

1. Field of the Invention

The present invention relates to a method for producing a hydrogen-detection sensor, in addition to the sensor produced using this method.

The main application of the invention is in the field of thermoelectric solar power for the detection of the possible hydrogen produced as a result of the decomposition of the heat-carrying fluids used in this industry. The sensor developed is also recommended in applications which require the detection of small traces of hydrogen in a large variety of industrial environments.

2. Description of Related Art Including Information Disclosed Under 37 CFR 1.97 and 37 CFR 1.98

Although in the bibliography, both scientific and of patents, a great variety of hydrogen detection methods has been reported based on processes that measure the changes in conductivity in oxide semiconductors such as $ZnO$, $SnO_2$, $TiO_2$, etc., generally activated using the presence of metal particles capable of dissociating the molecular hydrogen (e.g. Pt, Pd, etc.), an essential drawback thereof is its necessity of having to operate at high temperatures (above ambient), which, in addition to requiring localised heating systems, poses the danger of inducing explosions if the hydrogen to detect is in the air or mixed with oxygen.

As a result of these drawbacks, in the state of the art there are hydrogen detection sensors which work at ambient temperature and are based on principles of a colour change (chromophore sensors) which do not have electrical circuits inclined to generate sparks capable of producing gas ignition. A typical way of achieving said colour changes consists of mixing an easily reducible oxide such as $WO_3$, $MO_3$, $ZnO$, etc. and particles of metals such as Pt, Pd, etc., capable of dissociating the hydrogen molecule at low temperatures. This conceptual approach has been the object of various works and has been claimed in patents such as JP2007155650-A, JP2011021911-A. A very important condition for the operating capacity of this type of systems is that the oxide has a high porosity to promote a broad contact between the gas (hydrogen in this case) and the oxide in question. This high porosity also enables that the more expensive element of the system, the metal (Pt, Pd, etc.), can be dispersed in the form of small particles thus decreasing the overall quantity to be used. These conditions have obliged the devices of the state of the art to use the oxide in the form of powder, which involves various difficulties in their processing and fixing on substrates, also preventing the use of optical detection methods that require non-light dispersible materials.

Dealing with these difficulties, patent WO 2009133997 claims the development of a sensor in the form of thin layers using magnetron sputtering techniques where an oxide such as $WO_3$ prepared in compact form is intercalated between a substrate and a continuous and compact layer of Pt—Pd also prepared using magnetron sputtering. This architecture enables that the oxide $WO_3$ changes colour when the outer layer of Pt—Pd is exposed to hydrogen, although it may be problematic when regulating the magnitude of the change in colour which, given the difficulty of diffusion through a compact layer, it would only occur in the atomic layers of the $WO_3$ in close contact with the metal layer.

In view of the above, the present invention proposes a new method for producing an $H_2$ sensor with the aim of resolving the drawbacks of the $H_2$ sensors existing in the state of the art.

The method disclosed in the present invention is a simple process which enables minimising costs, since it allows optimising the quantity of active metal necessary for producing the sensor, in addition to providing an $H_2$ sensor with the following advantages:

- It is capable of working at ambient temperature and up to around 550° C.
- It allows the optical detection of $H_2$ with the naked eye.
- It is a reversible sensor which changes colour in the presence of $H_2$ and returns to its normal state in the absence of said gas.
- It is an accumulative sensor the colour of which increases with exposure to $H_2$ gas, in addition to with the concentration of said gas.

BRIEF SUMMARY OF THE INVENTION

The present invention relates to a method for preparing a visual hydrogen sensor, i.e. which allows optical detection, with the naked eye, of hydrogen in a medium as a result of a change of colour in the sensor in the presence of said gas.

The method for producing the hydrogen sensor of the present invention comprises the following phases or stages:

Stage 1: Deposition of an active oxide on a substrate using physical vapour deposition (PVD). The deposition geometry is a glancing angle, preferably of between 60-90° (GLAD). This generates a porous layer of the oxide.

The active oxide is a compound that does not absorb visible light in its completely oxidised state, but it is coloured when partially reduced due to exposure to hydrogen atoms. This is as a result of the fact that metal cations present in the structure of the oxide may experience a reduction of its formal oxidation state from a high value to a lower one by its interaction with hydrogen and with the change in its oxidation state, the cations have light absorption within the range of the visible spectrum.

Said active oxide may be simple or mixed.

The active simple oxide is an oxide comprising a single metal element and which acquires a certain colouring when some cations of its structure are reduced after its exposure to hydrogen atoms.

Preferably, among the active simple oxides are metal oxides comprising a metal selected from among the groups IVB, VB, VIB, IIB, IIIA, IVA.

More preferably, among the active simple oxides deposited are the following: $WO_3$, $MoO_3$, $Ta_2O_5$, $TiO_2$, $ZnO$, $V_2O_5$, $SnO_2$ and $In_2O_3$.

The active mixed oxides are solid mixtures or solutions of an active simple oxide of the aforementioned type, with an optically neutral oxide in the visible. The neutral oxide does not have colouring after its exposure to hydrogen (it acts by way of a neutral and transparent matrix), such as $Al_2O_3$ or $SiO_2$ of groups IIIA, IVA of the periodical table and which are characterised in that they are not easily reducible by their interaction with hydrogen.

The active mixed oxides comprise, therefore, at least two different metal elements.

These mixed oxides are prepared, for example, by simultaneous evaporation and deposition of both oxides, the cations of both compounds are randomly integrated in a single network of oxygen anions with variable stoichiometrics of the type, for example, $Si_xW_yO_x$.

The incorporation of an optically neutral oxide such as $SiO_2$, $Al_2O_3$, etc. allows varying the optical properties of the layer of active simple oxide (refraction index) and the response type (magnitude of the transmittance change) to hydrogen exposure, in addition to stabilising its functioning at high temperature. In particular, the different proportion in the neutral oxide layer/active simple oxide may serve for producing visual sensors with different sensitivity to partial pressure and the dose of hydrogen to detect.

In these layers of mixed oxides, one of the cations changes colour on being reduced (e.g. $W^{6+}$ to $W^{5+}$, $W^{6+}$ to $W^{4+}$, $Mo^{6+}$ to $Mo^{5+}$, etc.) and the other is a cation which does not change its oxidation state and which is, therefore, neutral from the standpoint of changes in colour (e.g. $Al^{3+}$ or $Si^{4+}$).

An essential characteristic of the method of the present invention is the application of PVD methods (Physical Vapour Deposition) at glancing angles for preparing the oxide layer, since this technique allows obtaining a high porosity. In particular, as mentioned above, it considers the use of PVD methods in glancing angle configuration (GLAD) which, although it has been widely used for the synthesis of layers with optical functionality and other functional applications, has not been used to date for preparing gasochromic sensors.

Using the aforementioned geometric configuration during the deposition process, the layer microstructure is porous and is formed by a series of columns, more or less connected to one another and inclined towards the flow arrival direction. This porous structure, where large pores extend from the surface towards the substrate, allows a fast and effective diffusion of any gas of an ambient medium from the outside to all the interior of the layer. A similar effect, both in microstructure of the layer and in porosity, is achieved if the evaporation is carried out from two different targets of the two oxides which are mixed in the layer or of a mixed target of both oxides.

Using this deposition method, the layers obtained are very adherent to the substrates on which they are deposited, their thickness is easily controllable and they have singular gasochromic properties and responses which, in the case of using mixed oxides, are modulable.

The thickness of the oxide layer may vary from a few dozen nanometers to microns, now have sufficient optical sensitivity to the human eye for thicknesses of some hundreds of nanometers. This sensitivity increases with the layer thickness, a parameter which, however, also makes the device more expensive so that it is convenient to define the best conditions that optimise the perception capacity/cost ratio of the sensor.

Preferably, the thickness of the oxide layer deposited is less than one micron, and more preferably between 200 and 600 nm.

Among the PVD techniques used are heat evaporation, electron bombarding and magnetron sputtering.

Ceramics, metals, plastics and paper can be used as a substrate.

Stage 2: Preparation of a solution of a precursor compound of an active metal (capable of dissociating the hydrogen molecule in its two constituent atoms at ambient temperature). The solution may also include a carrier vector, preferably which is calcined below 400° C. The carrier vector is integrated by a compound, generally polymeric whose purpose consists on carrying, in later stages, the precursor metal towards the interior of the oxide layer pores.

Among the precursors of the active metal, are the metal-organic compounds such as porphyrins which include in their core the active metal, in addition to salts (chlorides, nitrates, etc.).

The capacity for dissociating the hydrogen molecule is found in active metals such as Platinum (Pt) and Palladium (Pd), which are capable of generating $H_2$ dissociating processes even at ambient temperature. Therefore, preferably the active metals for this application are Pd and Pt.

The active metal precursor or precursors used as the carrier vector must be soluble in the solvent used to prepare the solution.

Preferably dichloromethane or acetone is used as solvent for preparing the solution.

As carrier vector is used preferably the polymer poly (methyl methacrylate) (PMMA). Preferably, the carrier vector is used in controlled concentration which may vary between 0.5 and 5% by weight. More preferably it is used in a concentration of 1% by weight.

It is sought that the quantity of active metal to be used is the minimum capable of dissociating the hydrogen molecule in its two constituent atoms at ambient temperature, thus managing to reduce costs. To do this, it is a necessary condition that the minimum possible quantity of metal incorporated is present in the form of nanoparticles of the smallest possible size.

Stage 3: Deposition of the solution prepared in stage 2 on the surface of the porous layer of oxide prepared in stage 1.

The spin coating method or dip coating method is preferably used to deposit the solution on the oxide layer. The spin coating method consists of depositing drops of the solution on the flat sample that rotates at high speed. Using the dip coating method, the oxide layer deposited on the corresponding substrate is immersed in the solution and extracted at controlled speed thereof. In both cases, after the evaporation of the solvent, the formation of a layer of the polymer compound which acts as carrier vector is promoted in the following stage of the process which, supported on the oxide layer, contains the required concentration of metal precursor molecules.

Stage 4: Inclusion or incorporation of the active metal precursor in the pores of the oxide layer prepared in stage 1, in addition to decomposition of the metal precursor and of the carrier vector. This inclusion and decomposition is carried out by heat or photochemical activation of the unit resulting from stage 3. This achieves the incorporation of molecules of the metal precursor or precursors of the active metals, (preferably Pt and/or Pd) inside the pores of the oxide layer. The heat activation is carried out at temperatures between 250 and 500° C., preferably 350° C. This heat treatment promotes that the carrier vector, in this case a polymeric compound, is introduced in the pores of the oxide layer carrying with it the precursor molecules of the active metals. In addition to achieving the carrying effect, the heating to the indicated temperature produces the decomposition and elimination of the compound which acts as carrier vector (preferably PMMA), the decomposition of the precursor molecule and the formation of small metal particles of the active metal distributed homogeneously throughout the layer thickness.

In the case of using substrates of paper or another material which do not withstand high temperatures, a photochemical activation is carried out. In this case a polymer is not used as carrier vector, instead the precursor molecule is directly incorporated in the pores on doing so in the solvent where it is dissolved. The precursor material is then activated using light. Using photochemically induced processes, the decomposition of the precursor molecules incorporated in the active layer pores occurs and nanoparticles of the corresponding metals are formed.

The use of porphyrin-type precursors and related makes it possible to achieve layers of great activity where the quantity of active metal, generally the most expensive component of the unit, is minimum and this is in the form of small particles. This is achieved thanks to the porphyrin having a highly controllable decomposition, which allows evaporating/decomposing the porphyrin fragments bound to the metal core once it has been carried within the column structure (porous) of the oxide layer. Given the large size of the porphyrin molecule, its use makes it possible to define a natural separation between the active metal atoms incorporated, thus minimizing the quantity used to generate nanoparticles.

The deposition process of stage 3 and the activation stage of stage 4 may be repeated as many times as desired if one wants to increase the quantity of active metal incorporated in the pores.

Another additional effect of the heat activation stage is to achieve that the final sensor layer is colourless. According to the experimental deposition conditions of the oxide layer, this may already have a certain colour, restoring its colourless appearance using the heat or photochemical activation process to which it is subjected in stage 4.

The sensor obtained using the aforementioned method may be immediately used as hydrogen sensor, either as single layer or incorporated in a more complex structure where an active layer is placed beside a neutral layer, white or of another colour or appearance so that, serving as contrast, it highlights the human eye's capacity for colour perception. Likewise, this sensor can be used with optical detection techniques based on the use of optical fibres or similar optical devices.

The object of the present invention is the hydrogen sensor produced using the aforementioned method.

The visual hydrogen sensor prepared using the process of the present invention is based on the observation of colour changes typically from white or colourless to blue colours, or, in general dark, whose intensity depends on the exposure dose. The degree of darkness may vary by changing the layer thickness, a parameter which may be adjusted to achieve maximum visual sensitisation with respect to the human eye.

It is a highly sensitive accumulative sensor which functions at ambient temperature or at high temperatures of up to 550° C. Its accumulative character responds to the fact that the colour intensity increases with the dose of hydrogen to which it has been exposed. In particular, the degree of colour increases with the hydrogen concentration in a medium and with exposure time. Using the described method it is possible to control the sensor's sensitivity range, mixing various proportions of the active oxide with the neutral oxide, thus being able to achieve layers which respond to various hydrogen dose ranges.

When the sensor coloured after its exposure to hydrogen is exposed to air without hydrogen, a slow reversal is reproduced of the coloured to colourless situation, a process which is reversible provided that the process is reproduced. The reversibility is also complete in the case of operating at high temperatures of up to 550° C. when a mixed oxide is used as base layer and limited to a few cycles in the case of using the simple oxides at that temperature. For operating temperatures of up to 200° C., all the sensors developed, irrespective of whether they are based on layers of simple or mixed oxides, are reversible.

The sensor produced using the method of the present invention is not affected by exposure to sunlight, therefore being particularly suitable for solar technology applications.

The method described in the present invention has important advantages with respect to the methods and sensors described in the state of the art. In the present invention, the magnitude of the colour change (transmittance change) can be graduated in accordance with the composition of the mixed oxide used and directly related to the layer thickness used. The present invention has the advantages of the powder-based methods and that of the physical vapour deposition (PVD) methods, among them magnetron sputtering. The method of the invention allows preparing layers with a high specific surface, which provide a great increase in sensitivity and makes it possible to decrease the quantity of active metal to incorporate in the gasochromic system, giving layers of oxides that are not light dispersible, with the possibility of using optical detection methods based on optical fibres or similar and also preserving merely visual detection.

The new method, adapted to the thin-layer topology, allows the regulated incorporation of pure metal particles (Pt, Pd, etc.) or alloys thereof, where the particle size, their homogeneous distribution throughout the layer thickness and the overall amount of metal, can be controlled with great precision. Another of the advantages of the method developed is that it loses practically nothing of the metal precursor or precursors used, giving rise to particles of very small size which maximise the catalytic effect of rupture of the hydrogen molecule when it is adsorbed on the metal surface.

BRIEF DESCRIPTION OF THE DRAWINGS

To complement the description being made and with the object of aiding toward a better understanding of the invention, a set of drawings is attached where the following has been represented with an illustrative and non-limiting character.

DETAILED DESCRIPTION OF THE INVENTION

To achieve a better understanding of the invention, a preferred embodiment of the method described for preparing a gasochromic $H_2$ sensor is described below.

Figure 1:
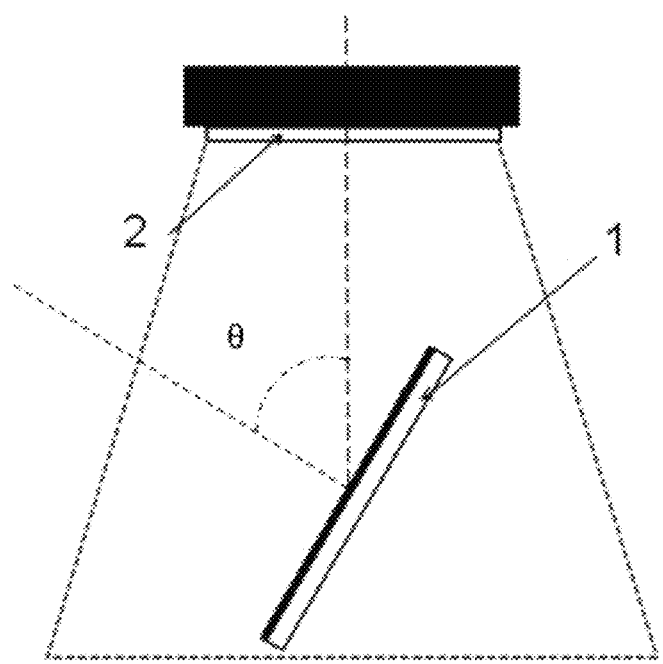
FIG. 1.—Diagram of a physical vapour deposition (PVD) process, glancing angle evaporation where the substrate is represented by reference (1) and the cathode by reference (2).

Stage 1: In first place, the deposition is carried out of a layer of $WO_3$ on a quartz substrate (1). This deposition is carried out using the magnetron sputtering technique for a deposition angle (θ of 80°, with this measured from the perpendicular to the substrate to the direction perpendicular to the magnetron target (see FIG. 1). The magnetron sputtering process conditions used are:

Residual pressure of $10^{-6}$ mbar
Working pressure of $5.10^{-3}$ mbar
A mixture of gases of 20 sccm of Ar (inert gas)+5 sccm of $O_2$ (reactive gas)
Source power: 125 w
Tungsten target or cathode (2).

A mixed oxide could alternatively be deposited: Six-WyOx, consisting of a mixture of the oxides $WO_3$ and $SiO_2$. The magnetron sputtering technique would also be performed for a deposition angle of 80°, with the following conditions:

Residual pressure of $10^{-6}$ mbar
Working pressure of $5·10^{-3}$ mbar
A mixture of gases of 40 sccm of Ar (inert gas)+5 sccm of $O_2$ (reactive gas)
Source power: 100 w
Tungsten and silicon mixed target or cathode (2), or two separate targets one of tungsten and another of silicon.

In a preferred embodiment of the invention, the thickness of the oxide layer deposited is of 400 nm.

Figure 3:
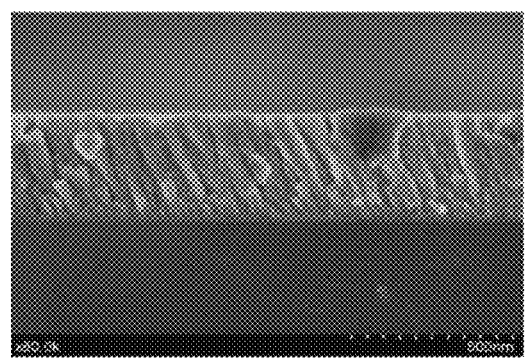
FIG. 3.—View of a cross-section of a $WO_3$ film prepared using glancing angle magnetron sputtering.

An image of the cross section of a $WO_3$ film showing its column microstructure may be observed in FIG. 3

Stage 2: Preparation of a $10^{-3}$ M solution of porphyrin with platinum core (Pt) and PMMA (1% by weight) in dichloromethane ($CH_2Cl_2$).

Stage 3: Deposition of the solution prepared in stage 2 on the surface of the porous layer of oxide prepared in stage 1 using a spin coating method. This achieves the evaporation of the solvent and the deposition of a layer of PMMA on the active layer of the porous oxide with a controlled concentration, typically of around $10^{16}$-$10^{17}$ atoms per cm² of metal atoms.

Stage 4: Inclusion or incorporation in the pores of the active metal precursor, in addition to decomposition of the porphyrins with Pt core and the PMMA polymer using heat treatment at around 350° C. This also achieves elimination of the PMMA and the formation of metal nanoparticles of the active metal.

The distribution of Pt resulting throughout the thickness of the oxide layer is homogenous according to RBS (Rutherford Back Scattering) measurements.

Figure 2:
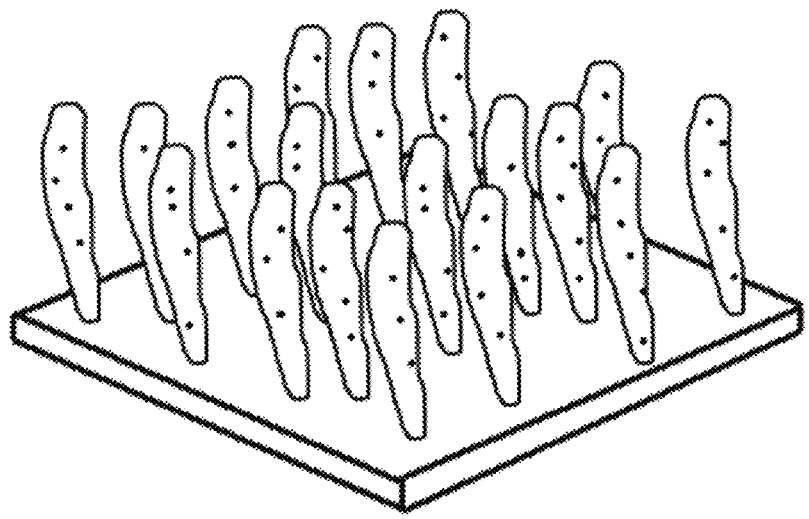
FIG. 2.—Diagram of a column layer of an oxide prepared using glancing angle evaporation, which includes metal nanoparticles in the layer pores.

After applying the previous drying and decomposition processes of the Pt precursor, the sensor is ready for use, giving rise to pores in the nanoparticle layer of 10 nm or less in size (see FIG. 2), according to measurements using TEM (Transmission electron Microscopy).

Figure 4:
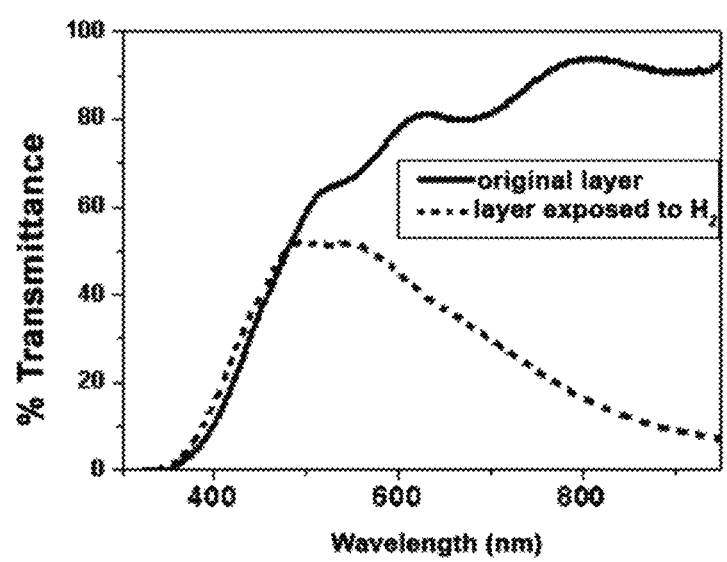
FIG. 4.—Optical response (transmittance spectrums) of a Pt/WO₃ sensor before (solid line) and after (broken line) being exposed to hydrogen.

When the sensor comes into contact with a gas containing hydrogen, said sensor begins to take on an increasingly blue colour as the exposure dose increases (exposure time and hydrogen concentration in the gas phase). FIG. 4 shows the change undergone in its transmittance before and after exposure to hydrogen.

In these working conditions, a sensor is directly obtained which does not have colouring once prepared, meaning that it may be used directly for the visual or optical detection of hydrogen.

The invention claimed is:

1. A method for producing a hydrogen-detection sensor, the method comprising:
    depositing a layer of $WO_3$ on a quartz substrate by sputtering with a magnetron with a deposition angle of 80° as measured from a direction perpendicular to the quartz substrate to a direction perpendicular to a target of the magnetron;
    preparing a solution of $10^{-3}$M of porphyrin with a platinum core and a poly(methyl methacrylate) (PMMA) of 1% concentration in dichloromethane;
    depositing the prepared solution onto a surface of the deposited layer of $WO_3$ on the substrate by spin coating; and
    including platinum in pores of the deposited layer of $WO_3$ on the quartz substrate by heat treatment at 350° C. of the prepared solution.

2. The method of claim 1, the sputtering by the magnetron being carried out at a residual pressure of $10^{-3}$ mbar, at a working pressure of $5·10^{-3}$ mbar, a mixture of 20 sccm of argon and 5 sccm of oxygen at a source power of 125 watts, and having either a tungsten target or a cathode.

3. A method for producing a hydrogen-detection sensor, the method comprising:
    depositing an active mixed oxide of $WO_3$ and $SiO_2$ using sputtering by a magnetron with a deposition angle of 80° as measured from a direction of perpendicular to a substrate to a direction perpendicular to a target of the magnetron;
    preparing a solution of $10^{-3}$M of porphyrin with a platinum core and a poly(methyl methacrylate) (PMMA) of 1% concentration in dichloromethane;
    depositing the prepared solution onto a surface of the deposited active mixture of $WO_3$ and $SiO_2$ by spin coating; and
    including platinum in pores of the deposited active mixed oxide of $WO_3$ and $SiO_2$ by heat treatment at 350° C. of the prepared solution.

4. The method of claim 3, the sputtering being carried out at a residual pressure of $10^{-6}$ mbar, at a working pressure of $5·10^{-3}$ mbar, with a mixture of 40 sccm of argon and 5 sccm of oxygen, with a source power of 100 watts, a target or a cathode in which the target is a mixture of tungsten or silicon or two separate targets in which one target is tungsten and the other target is silicon.

* * * * *